(12) United States Patent
Fujii et al.

(10) Patent No.: US 8,568,688 B2
(45) Date of Patent: Oct. 29, 2013

(54) AEROSOL FOR CONTROLLING INSECT PESTS

(75) Inventors: Shingo Fujii, Toyohashi (JP); Miho Iduhara, Hatsukaichi (JP); Shigeki Takaki, Hatsukaichi (JP); Masaaki Sugiura, Hatsukaichi (JP); Kazuyuki Ikeda, Hatsukaichi (JP)

(73) Assignee: Fumakilla Limited, Tokyo (JP)

( * ) Notice: Subject to any disclaimer, the term of this patent is extended or adjusted under 35 U.S.C. 154(b) by 1092 days.

(21) Appl. No.: 10/564,156

(22) PCT Filed: Aug. 4, 2004

(86) PCT No.: PCT/JP2004/011508
§ 371 (c)(1),
(2), (4) Date: Jan. 11, 2006

(87) PCT Pub. No.: WO2005/013685
PCT Pub. Date: Feb. 17, 2005

(65) Prior Publication Data
US 2006/0182774 A1    Aug. 17, 2006

(51) Int. Cl.
*A61K 51/00* (2006.01)
*A61K 36/14* (2006.01)

(52) U.S. Cl.
USPC .......................... 424/1.13; 516/1; 222/146.3

(58) Field of Classification Search
USPC .................... 424/405, 1.13; 222/146.3; 516/1
See application file for complete search history.

(56) References Cited

U.S. PATENT DOCUMENTS 6,695,227 B1 *   2/2004   Hayashi et al. ............... 239/337

FOREIGN PATENT DOCUMENTS

| EP | 0 897 755 A2 | 2/1999 |
|---|---|---|
| JP | 46-20837 | 6/1971 |
| JP | 59-175403 A | 10/1984 |
| JP | 1-190609 A | 7/1989 |
| JP | 4-120003 A | 4/1992 |
| JP | 5-294372 A | 11/1993 |
| JP | 9-67204 A | 3/1997 |
| JP | 9-175905 A | 7/1997 |
| JP | 2003-12422 A | 1/2003 |
| WO | WO-94/03056 A1 | 2/1994 |

OTHER PUBLICATIONS

Japanese Office Action dated Oct. 1, 2012 for Japanese Application No. 2005-513000.
Tsuda, "Relationship between Physical Properties of Aerosol Formulation and Its Insecticidal Efficacy", Journal of Pesticide Science, vol. 16, No. 3, pp. 533-543, Aug. 1991.

* cited by examiner

*Primary Examiner* — Fereydoun G Sajjadi
*Assistant Examiner* — Danielle Sullivan
(74) *Attorney, Agent, or Firm* — Birch, Stewart, Kolasch & Birch, LLP (57) ABSTRACT

An aerosol for disinsectization comprising a mixture comprising a disinfestant component, a solvent, and a propellant, and a pressure-resistant container provided with an actuator, wherein the mixture is contained in the pressure-resistant container, and wherein the solvent is contained in the mixture in an amount of from 0 to 10% by volume, and the actuator has an orifice diameter of from 0.7 to 2 mm; and an aerosol for disinsectization comprising a mixture comprising a disinfestant component, a solvent, and a propellant, and a pressure-resistant container provided with an actuator, wherein the mixture is contained in the pressure-resistant container, and wherein the solvent is contained in the mixture in an amount of from 0 to 10% by volume, and the actuator has a long nozzle having an orifice diameter of from 0.4 to 2 mm.

5 Claims, 3 Drawing Sheets

AEROSOL FOR CONTROLLING INSECT PESTS

TECHNICAL FIELD

The present invention relates to an aerosol for disinsectization having low pollution property.

BACKGROUND ART

An aerosol for disinsectization against, for instance, fly, mosquito, and cockroach is such that mainly a disinfestant component is dissolved in a solvent, and the solution together with a propellant such as liquefied petroleum gas (LPG) and dimethyl ether (DME) is filled in a pressure-resistant container. For example, the aerosol is used by spatially spraying or directly spraying to a subject harmful insect flying in a space such as living room. Alternatively, the aerosol is used by directly spraying to a subject harmful insect which crawls over a floor, or is used by spraying on a floor in advance to disinfest a subject harmful insect which creeps thereon.

However, after spraying, stickiness of a solvent remains on a curtain and a floor, and surrounding pollution upon disinsectization becomes a problem. In order to avoid such pollution, reduction in an amount of a solvent in an aerosol is considered to be effective. However, an amount of a solvent greatly influences on efficacy of an aerosol for disinsectization, and the efficacy is extremely decreased when the amount is reduced. Therefore, it is generally difficult to reduce the amount of a solvent.

In view of the above, the lowering of pollution property has been tried by devising a solvent. For example, use of a fluorocarbon-based solvent, a water-based solvent, pentane, isopentane or the like as a solvent has been proposed (for instance, see Japanese Patent Laid-Open Nos. Sho 59-175403, Hei 1-190609, and Hei 4-120003). On the other hand, an aerosol of which jetting force is enhanced to lower an amount of a solvent, which is used mainly for space spraying, has been also proposed (see Japanese Examined Patent Publication No. Sho 46-20837). However, an extent of low pollution property and its usability are not sufficient in some cases.

DISCLOSURE OF INVENTION

An object of the present invention is to provide an aerosol for disinsectization, which has high disinsectization efficacy and low pollution property.

Specifically, the present invention relates to:

[1] an aerosol for disinsectization comprising a mixture comprising a disinfestant component, a solvent, and a propellant, and a pressure-resistant container provided with an actuator, wherein the mixture is contained in the pressure-resistant container, and wherein the solvent is contained in the mixture in an amount of from 0 to 10% by volume, and the actuator has an orifice diameter of from 0.7 to 2 mm;

[2] an aerosol for disinsectization comprising a mixture comprising a disinfestant component, a solvent, and a propellant, and a pressure-resistant container provided with an actuator, wherein the mixture is contained in the pressure-resistant container, and wherein the solvent is contained in the mixture in an amount of from 0 to 10% by volume, and the actuator has a long nozzle having an orifice diameter of from 0.4 to 2 mm;

[3] the aerosol according to the above [1] or [2], wherein a pressure in the pressure-resistant container is from 0.15 to 0.4 MPa as expressed by a gauge pressure at 25° C.;

[4] the aerosol according to any one of the above [1] to [3], wherein a spraying amount is from 0.8 to 3 g/sec (25° C.);

[5] the aerosol according to any one of the above [1] to [4], wherein the solvent comprises a paraffinic hydrocarbon,

[6] the aerosol according to any one of the above [1] to [5], wherein the disinfestant component is at least one member selected from the group consisting of metofluthrin, phthalthrin, d-T80-phthalthrin, d,d-T80-prallethrin, d,d-T98-prallethrin, d-T80-resmethrin, transfluthrin, imiprothrin, cyphenothrin and d,d-T-cyphenothrin; and

[7] the aerosol according to any one of the above [1] to [6], wherein an average particle diameter of a particle comprising a sprayed aerosol content is from 15 to 45 μm (25° C.) at a position of a straight line distance from an orifice of 150 cm.

According to the present invention, a subject harmful insect can be disinfested without substantially polluting the surrounding with a solvent.

BEST MODE FOR CARRYING OUT THE INVENTION

The aerosol for disinsectization (hereinafter referred to as aerosol) of the present invention is an aerosol comprising a mixture comprising a disinfestant component, a solvent and a propellant (hereinafter referred to as aerosol composition), and a pressure-resistant container provided with an actuator, wherein the mixture is contained in the pressure-resistant container, and one of the significant features of the present invention resides in that the solvent is contained in the mixture in an amount of from 0 to 10% by volume, and the actuator has an orifice diameter of from 0.7 to 2 mm.

Usually, when the solvent is contained in an aerosol composition approximately in the range as defined in the present invention, a disinsectization efficacy is extremely reduced. Therefore, the present inventors have intensively continued to study reduction in the amount of the solvent contained which has been a serious problem in the development of an aerosol having low pollution property. As a result, the present inventors have found out for the first time that low pollution property can be achieved by spraying such the composition through an actuator having a specified orifice diameter, and further adjusting a pressure in a pressure-resistant container and an amount of spraying, even when the solvent contained in an aerosol composition is in a small amount, and whereby a sufficient disinsectization efficacy can be surprisingly maintained.

Specifically, some aerosol agents which can substantially prevent pollution with a spraying solution by reducing an amount of a solvent have been so far known (for instance, Japanese Patent Laid-Open Nos. Sho 59-175403 and Hei 4-120003, and Japanese Examined Patent Publication No. Sho 46-20837). However, conventionally, it has been considered that it is necessary to spray an aerosol content into a fine particle to enhance diffusively into a space and permeability into a gap between objects, in order to exhibit disinsectization efficacy by spraying in a space. Therefore, even if an amount of a solvent could be reduced, in order to secure formation of an aerosol content into a fine particle at spraying, it has been necessitated to make an orifice diameter of an actuator small, and increase a container inner pressure of an aerosol to increase an instant spraying force. However, in the method described above, even if diffusibility into a space can be secured, it is difficult to control a particle diameter, so that reduction in adhesion to an insect body cannot be avoided, and in particular, efficacy when directly sprayed to a harmful insect is not sufficiently exhibited. However, the present inventors have newly found out that diffusibility in a space and adhesion to an insect body can be maintained by adjusting an orifice diameter of an actuator, a pressure in a pressure-resistant container, a spraying amount or the like to control a particle diameter of a sprayed particle in a predetermined range, even if a solvent amount were reduced, so that a sufficient disinsectization efficacy satisfying both of space spraying and direct spraying is obtained. Then, the present inventors has accomplished the development of an aerosol of the present invention as an entirely new aerosol which can satisfy such the conditions. Therefore, an embodiment of reduction in an amount of the solvent in the present invention has not been so far specifically reported and cannot be expected at all from the prior art.

Herein, "low pollution property" refers to a nature of not being sticky due to a solvent remaining on a curtain, a floor or the like after spraying of an aerosol, or a nature of being rapidly dried even if a solvent remains in a slight amount, that is, nature of remarkably reduced stickiness due to a solvent.

The disinfestant component used in the present invention is not particularly limited. Examples include pyrethroid insecticide components such as metofluthrin (trade name: Eminence, same hereinafter), dl,d-T80-allethrin (Pynammin forte), phthalthrin (Neopynamin), d-T80-phthalthrin (Neopynamin forte), d,d-T80-prallethrin (Etoc), d,d-T98-prallethrin (98Etoc), d-T80-resmethrin (Crysron forte), transfluthrin (Biothrin), imiprothrin (Pralle), etofenprox (Trebon), cyphenothrin (Gokilaht), d,d-T-cyphenothrin (Gokilaht S), empenthrin (Vaporthrin), permethrin (Eksmin), phenothrin (Sumithrin), and pyrethrin (chrysanthemum Expale), organophosphate insecticide components such as fenitrothion (Sumithion) and malathion (Malathon), carbamate insecticide components such as propoxur (Baygon) and carbaryl (NAC), essential oils such as cassia oil, clove oil, hiba oil, cedar wood oil, cinnamon leaf oil, pimento oil, thyme oil, citronella oil and lemongrass oil, and repellent components such as diethyltolamide (DET). These components can be used alone, or in admixture of two or more, depending on utility. Inter alia, from the viewpoint of high safety and a high disinsectization efficacy, at least one member selected from the group consisting of metofluthrin, phthalthrin, d-T80-phthalthrin, d,d-T80-prallethrin, d,d-T98-prallethrin, d-T80-resmethrin, transfluthrin, imiprothrin, cyphenothrin and d,d-T-cyphenothrin is preferably used. The amount of the disinfestant component is contained in the aerosol composition is not particularly limited, and the amount is preferably from 0.0001 to 2% by weight/volume, more preferably from 0.001 to 1% by weight/volume.

The solvent is not particularly limited. The solvent includes, for example, hydrocarbons such as aliphatic hydrocarbon, aromatic hydrocarbon and alicyclic hydrocarbon, alcohols such as ethanol, isopropanol and methanol, esters such as fatty acid ester, vegetable oils, animal oils, and water. Inter alia, from the viewpoint of being excellent in efficacy, and inexpensive, the aliphatic hydrocarbons are preferably used. Further, among the aliphatic hydrocarbons, a paraffinic hydrocarbon (linear or branched saturated hydrocarbon), inter alia, normal paraffin (n-paraffin) is preferably used.

The solvent is contained in the aerosol composition in an amount of from 0 to 10% by volume from the viewpoint of low pollution property. In other words, in order to achieve low pollution property, the amount of the solvent is at most 10% by volume. From the viewpoint that a disinsectization efficacy is more highly exhibited, the amount of the solvent is preferably from 1 to 10% by volume. In addition, from the viewpoint that good balance of low pollution property and disinsectization efficacy is maintained, the amount is more preferably from 1 to 8% by volume, even more preferably from preferably 1 to 5% by volume, particularly preferably from 1 to 4% by volume, even more particularly preferably from 1 to 3% by volume.

The propellant is not particularly limited. From the viewpoint of easy availability and low cost, LPG (liquefied petroleum gas) and DME (dimethyl ether) are preferably used. The amount of the propellant contained in the aerosol composition is not particularly limited. The amount may be adjusted such that the amount of the propellant makes up 100% by volume together with a disinfestant component, a solvent, and optionally added other components described below, which constitute the composition. Here, the propellant occupies the balance of components other than the propellant, in the constituents of the aerosol composition.

The other components besides the above-mentioned components, which are optionally added to the aerosol composition of the present invention, include, for example, a surfactant, a synergist, an antioxidant, a fungicide, a perfume, an inert gas and the like. The amount of other components contained in the aerosol composition is not particularly limited. The other components may be contained in such amount that effect of the components can be exhibited in such a range that would not hamper the exhibition of the desired effect of the present invention.

A particularly preferable embodiment of the aerosol composition of the present invention is a composition in which a disinfestant component is from 0.001 to 1% by weight/volume, a solvent is from 1 to 4% by volume, other components are from 0 to 2% by weight/volume, and a propellant is the balance.

The aerosol of the present invention can be prepared by the same process as that for the known aerosol. For example, the method includes a process of injecting a stock solution containing a disinfestant component, a solvent and, optionally, other components into a pressure-resistant container provided with an actuator, and then filling a propellant thereinto under reduced pressure, and a process of injecting a disinfestant component, a solvent and, optionally, other components into the container separately, and filling a propellant thereinto under reduced pressure.

The pressure-resistant container provided with an actuator which is used in the present invention is, for example, such that a known actuator having a predetermined orifice diameter is attached to a known aerosol can. Herein, the "orifice diameter" refers to an inner diameter of a final part of an actuator (hole diameter of actuator) when an aerosol content is sprayed (discharged) to the outside.

From the viewpoint of exhibition of the desired effect of the present invention, the actuator has an orifice diameter of from 0.7 to 2 mm, preferably from 0.8 to 2 mm. From the viewpoint of greater exhibition of disinsectization efficacy, the actuator has an orifice diameter of more preferably from 1 to 1.8 mm, even more preferably from 1.2 to 1.6 mm.

In addition, as one embodiment of the present invention, there can be provided an aerosol having the same constitutions as those of the above-mentioned aerosol except that an actuator has a long nozzle having an orifice diameter of from 0.4 to 2 mm. Such the aerosol can be prepared by using an actuator having a long nozzle having a predetermined orifice diameter in place of an actuator used in the above-mentioned aerosol.

In the actuator having a long nozzle, a final part of the actuator when an aerosol content is sprayed (discharged) to the outside means an external tip of a long nozzle (that is, a tip of a nozzle opposite to an actuator body), and an inner diameter of the tip (a hole diameter of an external tip of a long nozzle) corresponds to an orifice diameter. For example, even in the case where a long nozzle is such that its inner diameter mid way of a nozzle is changed in a few stages, an orifice diameter is an inner diameter of an external tip of a nozzle, and an inner diameter mid way of a nozzle is arbitrary. From the viewpoint of exhibition of the desired effect of the present invention, the aerosol of the present embodiment has an orifice diameter of from 0.4 to 2 mm, preferably from 0.45 to 2 mm. From the viewpoint of greater exhibition of disinsectization efficacy, the aerosol has an orifice diameter of more preferably from 0.8 to 1.5 mm.

The nozzle length of a long nozzle is not particularly limited. From the viewpoint of greater exhibition of disinsectization efficacy, the nozzle length is preferably from 0.5 to 15 cm. In addition, the form of a nozzle part is not particularly limited, and may be, for example, stretchable. In the case of stretchable nozzle, the nozzle length refers to a length in the stretched state. A material for a nozzle is also not particularly limited. The material includes, for example, polyethylene, polypropylene, Teflon, polyvinyl chloride, ABS (acrylonitrile-butadiene-styrene copolymer), stainless steel, aluminum and the like. From the viewpoint of moldability and cost, polyethylene and polypropylene are preferable as a material for a nozzle.

Generally, when an actuator has a long nozzle, disinsectization efficacy is excellent as compared with the case where an actuator is without a long nozzle. However, when an orifice diameter of an actuator is approximately 1.3 mm or larger, there is a tendency that a difference in the efficacy becomes small between the cases of the presence and the absence of a long nozzle. Therefore, in such the case, from the viewpoint of economical advantage, it is preferable to use an actuator without a long nozzle.

The number of orifices in the aerosol of the present invention is not particularly limited regardless of the presence or the absence of a long nozzle, as far as any one of orifices has an orifice diameter in the above-mentioned range. From easy molding of an actuator, the number of orifices is preferably 1 or 2. An orifice in the case where an actuator has a long nozzle refers to a hole of an external tip of a long nozzle. The details are as described above.

The material of the aerosol can used as a pressure-resistant container in the aerosol of the present invention is not particularly limited. The material includes, for example, tinplate, aluminum and the like. A content amount thereof is not particularly limited, and one having a content amount of usually, from 150 to 600 mL or so is suitably used.

The pressure in the pressure-resistant container containing the aerosol composition (container inner pressure) varies depending on solubility of a propellant in a solvent, a ratio occupied by a solvent, and so on. From the viewpoint of enhancement of exhibition of disinsectization efficacy, the pressure is preferably from 0.15 to 0.4 MPa, more preferably from 0.2 to 0.35 MPa, as expressed by a gauge pressure at 25° C. The range defined by arbitrarily combining an upper limit and a lower limit of these ranges is also a preferable range. A suitable pressure in a pressure-resistant container can be usually obtained by adjusting contents of a propellant or the like in the above-mentioned preferable ranges. Alternatively, for instance, the pressure in a pressure-resistant container may be appropriately adjusted using an inert gas such as a nitrogen gas and a carbon dioxide gas. A gauge pressure can be measured by a Bourdon-tube pressure gauge.

Thus, the aerosol of the present invention can be obtained. A spraying amount of the aerosol of the present invention (spraying amount of aerosol content) is not particularly limited. Usually, the spraying amount of 0.8 g/sec or larger at 25° C. is preferable. From the viewpoint of satisfying both of low pollution property and high disinsectization efficacy, the spraying amount of from 1 g/sec to 3 g/sec is more preferable. Therefore, as a spraying amount, usually, from 0.8 to 3 g/sec is preferable. When the aerosol is prepared by using respective components of the aerosol of the present invention in a preferable range as described above, usually, a spraying amount can be in a preferable range. In addition, in the aerosol of the present invention, when an aerosol content is sprayed, an average particle diameter of a particle composed of the content (sprayed particle diameter) is preferably from 15 to 45 μm (25° C.), more preferably from 18 to 36 μm (25° C.) at a position having a straight line distance from an orifice of 150 cm. In the aerosol of the present invention, the size of such a particle is effective for exhibiting disinsectization efficacy. Herein, an average particle diameter can be measured with a particle size distribution measuring apparatus (laser light scattering format, LDSA-1400A manufactured by Tonichi Computer Applications Co., Ltd.). A straight line distance from an orifice refers to a straight line distance from the center of an orifice in the orifice plane. In addition, the aerosol content refers to all components contained in a pressure-resistant container including a propellant when referred to a spraying amount. On the other hand, in the case of particle size determination, since the propellant gradually vaporizes as the aerosol content is off from the orifice, the propellant may not be included in the components of the content of the sprayed particle in some cases.

The aerosol of the present invention contains a solvent in a small amount and has low pollution property, and can effectively adhere a disinfestant component to a subject harmful insect, whereby disinsectization efficacy can be sufficiently exhibited.

As the aerosol of the present invention, various embodiments can be provided. As the aerosol of the present invention, an aerosol in which the solvent is contained in the aerosol composition in an amount of from 0 to 10% by volume, the orifice diameter of an actuator (without a long nozzle) is from 0.7 to 2 mm, and a pressure in a pressure-resistant container is from 0.15 to 0.4 MPa as expressed by a gauge pressure at 25° C. is preferable, and an aerosol in which the solvent is contained in the aerosol composition is from 0 to 10% by volume, an actuator has a long nozzle having an orifice diameter of from 0.4 to 2 mm, and a pressure in a pressure-resistant container is from 0.15 to 0.4 MPa as expressed by a gauge pressure at 25° C. is more preferable, in that any of low pollution property, disinsectization efficacy and economical efficacy are excellent.

A subject harmful insect of the aerosol of the present invention depends on a disinfestant component to be used. Examples of a subject harmful insect include flies such as house fly (*Musca domestica*), lesser housefly (*Fannia canicularis*) and flesh fly (*Sarcophaga peregrina*), mosquitoes such as common house mosquito (*Culex pipiens pallens*), house mosquito (*Culex pipiens molestus*) and Asian tiger mosquito (*Aedes albopictus*), cockroaches such as German cockroach (*Blattella germanica*), smoky-brown cockroach (*Periplaneta fuliginosa*) and American cockroach (*Periplaneta americana*), fleas such as human flea (*Pulex irritans*) and cat flea (*Ctenocephalides felis*), mites such as tropical rat mite (*Ornithonyssus bacoti*), mold mite (*Tyrophagus putrescentiae*), American house dust mite (*Dermatophagoides farinae*) and cheyletid mite (*Cheyletus malaccensis*), ants such as pharao ant (*Monomorium nipponense*), queenless-ant (*Pryistomymex pungens*) and Argentine ant (*Linepithema humile*), centipedes such as large centipede (*Sclopendra subspinipes mutilans*) and Japanese large centipede (*Scolopendra subspinipes japonica*), millipedes such as *Oxidus gracilis* and *Nedyopus tambanus*, isopodas such as sowbug (*Porcellio scaber*) and pillbug (*Armadilidium vulgare*), termites such as Japanese subterranean termite (*Reticulitermes speratus*) and Formosan subterranean termite (*Coptotermes formosanus*). Since the aerosol of the present invention has low pollution property, it is particularly preferably used indoor and, from such a viewpoint, as a subject harmful insect, flies, mosquitoes, cockroaches, fleas, mites, ants and centipedes are preferable.

EXAMPLES

The present invention will be explained in detail below on the basis of Examples, without intending to limit the present invention thereto. In the following Examples, a gauge pressure was measured with a Bourdon-tube pressure gauge. A spraying amount and a sprayed particle diameter of the aerosol are values at 25° C., and a sprayed particle diameter is determined at a position having a straight line distance from an orifice of 150 cm.

Test Example 1

Aerosols 1 to 9 (Examples 1 to 6 and Comparative Examples 1 to 3) satisfying the conditions shown in Table 1 were prepared. That is, aerosols 1 to 9 having predetermined aerosol compositions and having a container inner pressure [gauge pressure at 25° C.] of 0.4 MPa were prepared using an aerosol can having a content amount of 300 mL provided with an actuator having an orifice diameter of 0.8 mm without a long nozzle. The resulting aerosols 1 to 9 were evaluated for pollution property.

Pollution property was evaluated according to the following evaluation criteria by spraying an aerosol for 1 second from a position at 50 cm immediately above a central part of carbon paper (16.5 cm×23 cm), and visually examining the state of a solvent adhered to the carbon paper:

(Evaluation Criteria)
○: No wetting was observed.
Δ: Slight wetting was observed.
X: Clear wetting having a diameter of 10 cm or larger was observed.

The results for each of the aerosols are shown in Table 1.

TABLE 1

| No. | Aerosol | Components for Aerosol Composition | | | | Container Inner Pressure (MPa) | Orifice Diameter (mm) | Pollution Property |
|---|---|---|---|---|---|---|---|---|
| | | Disinfestant Component (% by weight/volume) | Solvent (% by volume) | | Propellant | | | |
| Ex. 1 | 1 | Neopynamin forte 0.15 | n-Paraffin | 0 | LPG Bal. | 0.4 | 0.8 | ○ |
| Ex. 2 | 2 | Neopynamin forte 0.15 | n-Paraffin | 1.67 | LPG Bal. | 0.4 | 0.8 | ○ |
| Ex. 3 | 3 | Neopynamin forte 0.15 | n-Paraffin | 3.33 | LPG Bal. | 0.4 | 0.8 | ○ |
| Ex. 4 | 4 | Neopynamin forte 0.15 | n-Paraffin | 5 | LPG Bal. | 0.4 | 0.8 | ○ |
| Ex. 5 | 5 | Neopynamin forte 0.15 | n-Paraffin | 6.67 | LPG Bal. | 0.4 | 0.8 | ○ |
| Ex. 6 | 6 | Neopynamin forte 0.15 | n-Paraffin | 10 | LPG Bal. | 0.4 | 0.8 | Δ |
| Comp. Ex. 1 | 7 | Neopynamin forte 0.15 | n-Paraffin | 13.3 | LPG Bal. | 0.4 | 0.8 | X |
| Comp. Ex. 2 | 8 | Neopynamin forte 0.15 | n-Paraffin | 16.7 | LPG Bal. | 0.4 | 0.8 | X |
| Comp. Ex. 3 | 9 | Neopynamin forte 0.15 | n-Paraffin | 26.7 | LPG Bal. | 0.4 | 0.8 | X |

It can be seen from the results of Table 1 that when the solvent is contained in the aerosol composition in an amount of 10% by volume or smaller, the aerosol has low pollution property.

Test Example 2

Aerosols 10 to 25 (Examples 7 to 18 and Comparative Examples 4 to 7) satisfying conditions shown in Tables 2 and 3 were prepared. That is, aerosols 10 to 18 having predetermined aerosol compositions and having a container inner pressure [gauge pressure at 25° C.] of 0.4 MPa were prepared using an aerosol can having a content amount of 300 mL provided with an actuator without a long nozzle having a predetermined orifice diameter, and aerosols 19 to 25 having predetermined aerosols compositions and having a container inner pressure [gauge pressure at 25° C.] of 0.4 MPa were prepared using the same aerosol can provided with an actuator with a long nozzle having a predetermined orifice diameter. A nozzle length was 10 cm.

Figure 1:
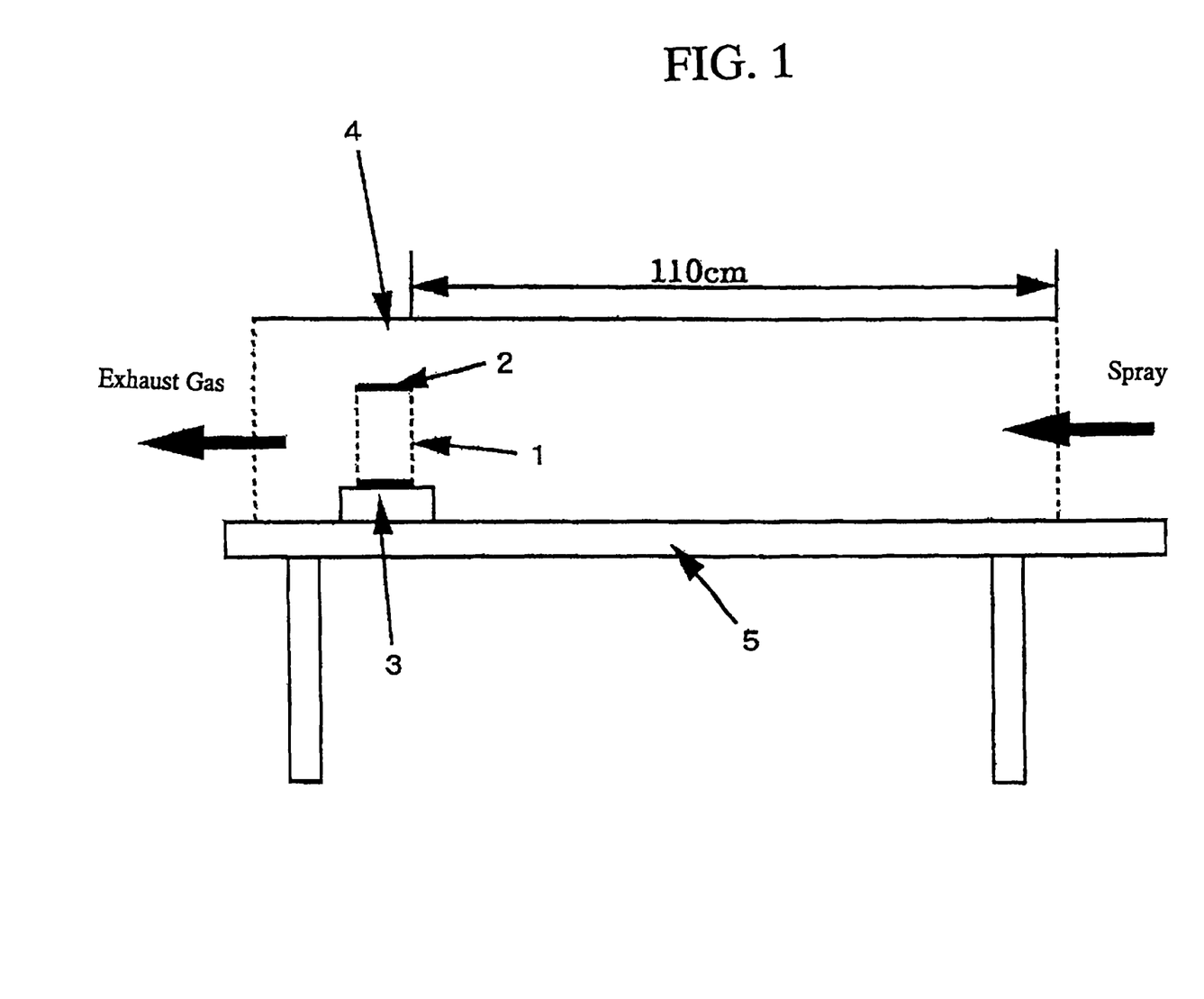
FIG. 1 is a schematic explanatory view for an apparatus used for evaluation of disinsectization efficacy of an aerosol.

The resulting aerosols 10 to 25 were evaluated for disinsectization efficacy. Disinsectization efficacy was evaluated by a direct spraying method. FIG. 1 shows an outline of an apparatus used upon evaluation. Test insects (6 house flies) were placed into a glass ring 2 (diameter 9 cm, height 6 cm) having both sides covered with a 16 mesh net 1, and an aerosol was sprayed from a distance (spraying distance) of 110 cm. The glass ring 2 is fixed on a base 3, and such base 3 is fixed at a prescribed position in a glass cylinder 4 (diameter: 20 cm). In addition, the glass cylinder 4 is fixed on a frame 5. A constant amount of a stead flow of the air is flown in the glass cylinder 4 towards a direction described as "Exhaust Gas" from a position described as "Spray" in FIG. 1, and thereby the sprayed aerosol contents hit at all of test insects. An amount of an aerosol to be sprayed was adjusted so that an amount of an active ingredient (Neopynamin forte) became constant (about 2 mg/time). Adjusting of an amount of an aerosol to be sprayed was performed by using an aerosol automatic fine amount spraying apparatus (manufactured by YASUDA SEIKI SEISAKUSHO LTD), wherein a spraying time of the apparatus is adjusted.

Figure 2:
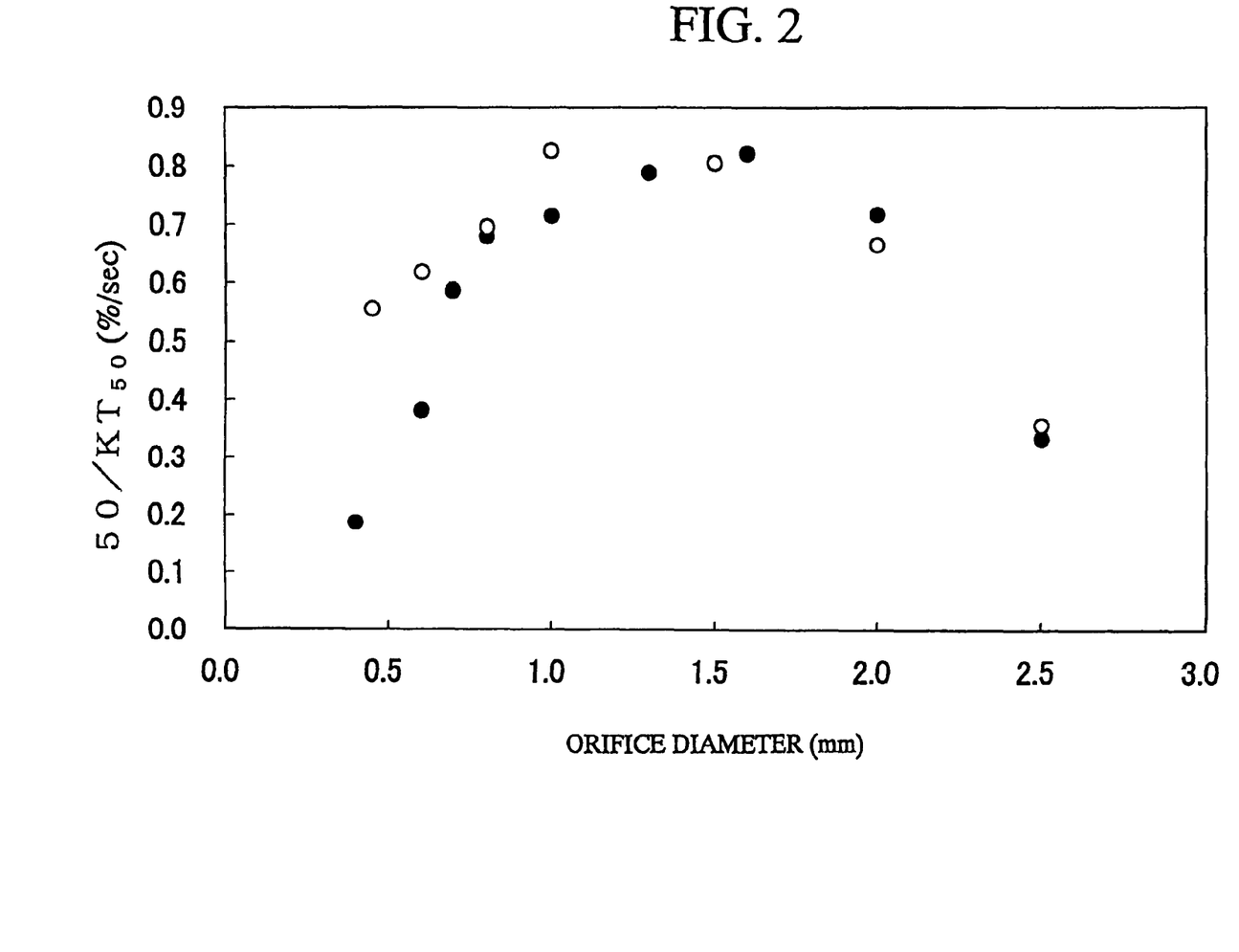
FIG. 2 is a graph showing evaluation results of disinsectization efficacy of an aerosol with or without a long nozzles wherein solid circles (●) are the results of the aerosol without a long nozzle, and open circles (○) are the results of the aerosol with a long nozzle.

The number of knocked down insect was counted with time, and $KT_{50}$ (sec) was obtained by a Probit method of Bliss. A smaller value shows that disinsectization efficacy of an aerosol is more excellent. In addition, a ratio of test insects knocked down per one second is expressed by multiplying an inverse of the resulting $KT_{50}$ with 50, and this was adopted as an average knock down rate ($50/KT_{50}$) (%/sec). A larger value shows that disinsectization efficacy of an aerosol is more excellent. An experiment was performed by repeating at least three times, and an average value was obtained. Results regarding respective aerosols in the case where there is no long nozzle are shown in Table 2, and results regarding respective aerosols in the case where there is a long nozzle are shown in Table 3. A graph was prepared by combining the results of Tables 2 and 3, and the graph is shown in FIG. 2.

orifice diameter exceeds 2 mm in both cases. Further, it is seen that disinsectization efficacy of an aerosol in the case with a long nozzle is improved as compared with the case without a long nozzle.

Test Example 3

Aerosols 26 to 34 (Examples 19 to 27) satisfying conditions shown in Table 4 were prepared. Specifically, aerosols 26 to 34 having predetermined aerosol compositions and container inner pressure [gauge pressure at 25° C.] were prepared using an aerosol can having a content amount of 300 mL provided with an actuator having an orifice diameter of 1.3 mm without a long nozzle. A container inner pressure was adjusted at filling of a propellant by adjusting an extent of reduced pressure in an aerosol can and, at the same time, blending an appropriate amount of LPGs having different pressures (LPG 0.15, LPG 0.28, LPG 0.4, LPG 0.5: a number is expressed by MPa at 20° C.).

TABLE 2

| No. | Aerosol | Components for Aerosol Composition | | | | Container Inner Pressure (MPa) | Orifice Diameter (mm) | $KT_{50}$ (sec) | $50/KT_{50}$ (%/sec) |
| | | Disinfestant Component (% by weight/volume) | Solvent (% by volume) | | Propellant | | | | |
|---|---|---|---|---|---|---|---|---|---|
| Comp. Ex. 4 | 10 | Neopynamin forte 0.15 | n-Paraffin | 0 | LPG Bal. | 0.4 | 0.4 | 267.5 | 0.187 |
| Comp. Ex. 5 | 11 | Neopynamin forte 0.15 | n-Paraffin | 0 | LPG Bal. | 0.4 | 0.6 | 130.9 | 0.382 |
| Ex. 7 | 12 | Neopynamin forte 0.15 | n-Paraffin | 0 | LPG Bal. | 0.4 | 0.7 | 85.2 | 0.587 |
| Ex. 8 | 13 | Neopynamin forte 0.15 | n-Paraffin | 0 | LPG Bal. | 0.4 | 0.8 | 73.5 | 0.68 |
| Ex. 9 | 14 | Neopynamin forte 0.15 | n-Paraffin | 0 | LPG Bal. | 0.4 | 1 | 70 | 0.714 |
| Ex. 10 | 15 | Neopynamin forte 0.15 | n-Paraffin | 0 | LPG Bal. | 0.4 | 1.3 | 63.4 | 0.789 |
| Ex. 11 | 16 | Neopynamin forte 0.15 | n-Paraffin | 0 | LPG Bal. | 0.4 | 1.6 | 60.9 | 0.821 |
| Ex. 12 | 17 | Neopynamin forte 0.15 | n-Paraffin | 0 | LPG Bal. | 0.4 | 2 | 69.8 | 0.716 |
| Comp. Ex. 6 | 18 | Neopynamin forte 0.15 | n-Paraffin | 0 | LPG Bal. | 0.4 | 2.5 | 150.1 | 0.333 |

TABLE 3

| No. | Aerosol | Components for Aerosol Composition | | | | Container Inner Pressure (MPa) | Orifice Diameter (mm) | $KT_{50}$ (sec) | $50/KT_{50}$ (%/sec) |
| | | Disinfestant Component (% by weight/volume) | Solvent (% by volume) | | Propellant | | | | |
|---|---|---|---|---|---|---|---|---|---|
| Ex. 13 | 19 | Neopynamin forte 0.15 | n-Paraffin | 0 | LPG Bal. | 0.4 | 0.45 | 89.6 | 0.558 |
| Ex. 14 | 20 | Neopynamin forte 0.15 | n-Paraffin | 0 | LPG Bal. | 0.4 | 0.6 | 80.6 | 0.62 |
| Ex. 15 | 21 | Neopynamin forte 0.15 | n-Paraffin | 0 | LPG Bal. | 0.4 | 0.8 | 71.9 | 0.695 |
| Ex. 16 | 22 | Neopynamin forte 0.15 | n-Paraffin | 0 | LPG Bal. | 0.4 | 1 | 60.6 | 0.825 |
| Ex. 17 | 23 | Neopynamin forte 0.15 | n-Paraffin | 0 | LPG Bal. | 0.4 | 1.5 | 62.1 | 0.805 |
| Ex. 18 | 24 | Neopynamin forte 0.15 | n-Paraffin | 0 | LPG Bal. | 0.4 | 2 | 75.1 | 0.666 |
| Comp. Ex. 7 | 25 | Neopynamin forte 0.15 | n-Paraffin | 0 | LPG Bal. | 0.4 | 2.5 | 140.2 | 0.357 |

Figure 3:
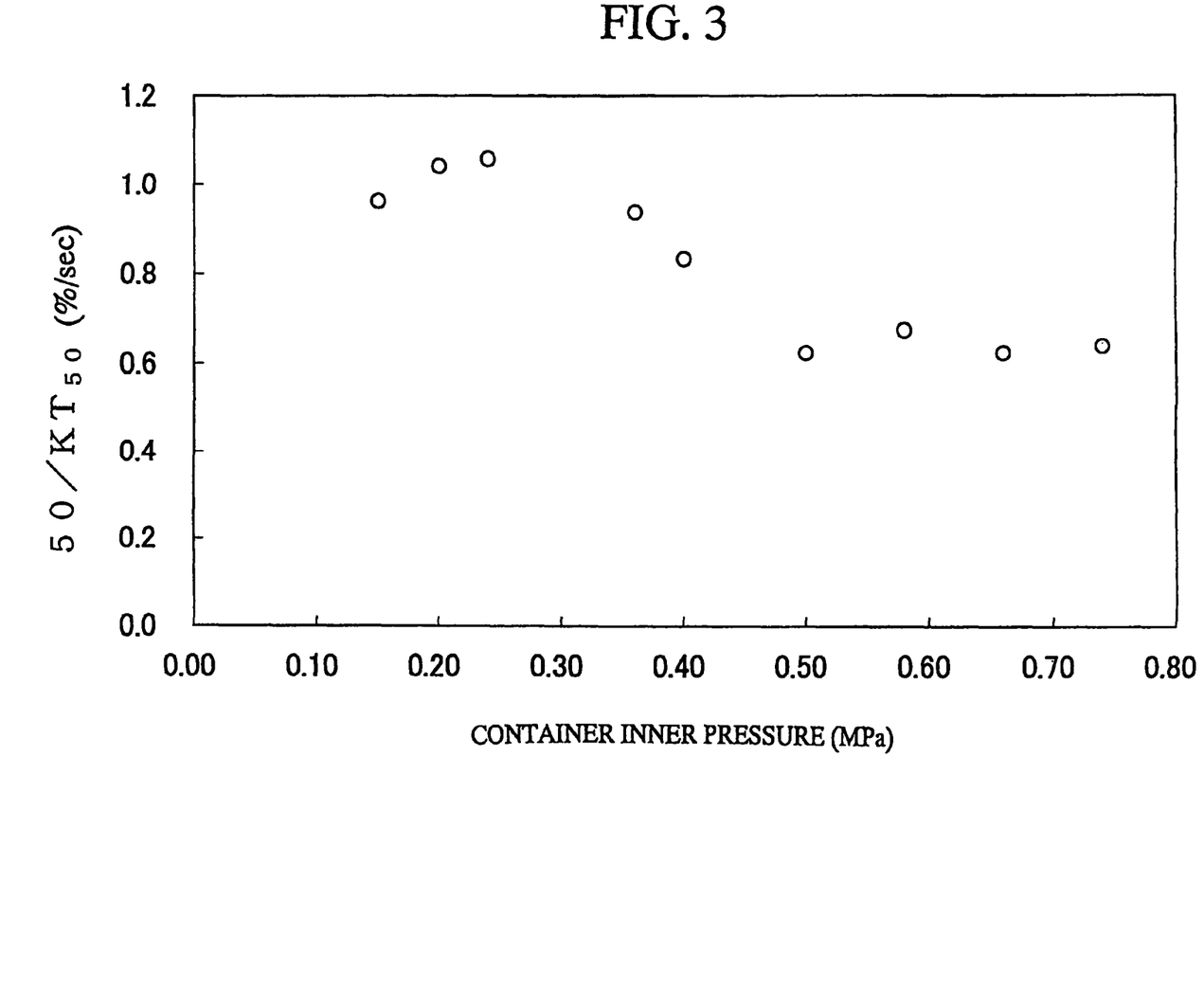
FIG. 3 is a graph showing evaluation results of disinsectization efficacy of an aerosol when inner pressure of a container varies.

It can be seen from the results of Tables 2 and 3 and FIG. 2 that an aerosol can exhibit high disinsectization efficacy, when an orifice diameter is 0.7 mm or larger in the case without a long nozzle, and when an orifice diameter is 0.4 mm or larger in the case with a long nozzle. In addition, it can be seen that disinsectization efficacy is deteriorated when an The resulting aerosols 26 to 34 were evaluated for disinsectization efficacy. Disinsectization efficacy was evaluated by obtaining $KT_{50}$ and $50/KT_{50}$ in the same manner as that of Test Example 2. Results are shown in Table 4. In addition, the results of Table 4 were graphed, and the graph is shown in FIG. 3.

TABLE 4

| No. | Aerosol | Disinfestant Component (% by weight/volume) | Solvent (% by volume) | | Propellant | | Container Inner Pressure (MPa) | Orifice Diameter (mm) | $KT_{50}$ (sec) | $50/KT_{50}$ (%/sec) |
|---|---|---|---|---|---|---|---|---|---|---|
| Ex. 19 | 26 | Neopynamin forte 0.15 | n-Paraffin | 0 | LPG | Bal. | 0.15 | 1.3 | 52 | 0.962 |
| Ex. 20 | 27 | Neopynamin forte 0.15 | n-Paraffin | 0 | LPG | Bal. | 0.2 | 1.3 | 48 | 1.042 |
| Ex. 21 | 28 | Neopynamin forte 0.15 | n-Paraffin | 0 | LPG | Bal. | 0.24 | 1.3 | 47.3 | 1.057 |
| Ex. 22 | 29 | Neopynamin forte 0.15 | n-Paraffin | 0 | LPG | Bal. | 0.36 | 1.3 | 53.4 | 0.936 |
| Ex. 23 | 30 | Neopynamin forte 0.15 | n-Paraffin | 0 | LPG | Bal. | 0.4 | 1.3 | 60 | 0.833 |
| Ex. 24 | 31 | Neopynamin forte 0.15 | n-Paraffin | 0 | LPG | Bal. | 0.5 | 1.3 | 80 | 0.625 |
| Ex. 25 | 32 | Neopynamin forte 0.15 | n-Paraffin | 0 | LPG | Bal. | 0.58 | 1.3 | 74 | 0.676 |
| Ex. 26 | 33 | Neopynamin forte 0.15 | n-Paraffin | 0 | LPG | Bal. | 0.66 | 1.3 | 80 | 0.625 |
| Ex. 27 | 34 | Neopynamin forte 0.15 | n-Paraffin | 0 | LPG | Bal. | 0.74 | 1.3 | 78 | 0.641 |

It can be seen from the results of Table 4 that all aerosols have sufficient disinsectization efficacy. In addition, it can be seen that an aerosol can exhibit higher disinsectization efficacy when a container inner pressure is 0.4 MPa or smaller, more preferably 0.3 MPa or smaller.

Test Example 4

Aerosols 35 to 38 having predetermined aerosol compositions containing 0.15% by weight/volume of disinfestant component (Neopynamin forte), a predetermined amount of a solvent (n-paraffin) shown in Table 5, and the balance a propellant (LPG), and having a container inner pressure [gauge pressure at 25° C.] of 0.15 MPa were prepared using an aerosol can having a content amount of 300 mL provided with an actuator having an orifice diameter of 1.3 mm with or without a long nozzle (1.5 cm) (Examples 28 to 31). In addition, aerosols 39 to 41 having aerosol compositions containing a prescribed amount of a solvent (n-paraffin) and the balance a propellant (LPG), and having a container inner pressure of 0.42 MPa were prepared using an aerosol can having a content amount of 300 mL provided with an actuator without a long nozzle having an orifice diameter of 0.65 mm (Comparative Examples 8 to 10). In particular, an aerosol 41 has approximately the same constitutions as those of the aerosols for disinsectization, which the present applicants have previously sold on a market, and this was positioned as a standard prior product.

The resulting aerosols 35 to 41 were evaluated for disinsectization efficacy. Disinsectization efficacy was evaluated by obtaining $KT_{50}$ in the same manner as that of Test Example 2. Results are shown in Table 5. Evaluation was performed using house flies and German cockroaches (10 each) as test insects, and was repeated at least three times. For the evaluation using the house flies, a spraying distance was 150 cm, and an amount of an aerosol to be sprayed was adjusted so as to give an active ingredient of about 1.2 mg/time, and for the evaluation using the German cockroaches, a spraying distance was 110 cm, and an amount of an aerosol to be sprayed was adjusted so as to give an active ingredient of about 5 mg/time.

TABLE 5

| | | | Spraying Amount (g/sec) | Sprayed Particle Diameter (μm) | House fly | | German cockroach | |
|---|---|---|---|---|---|---|---|---|
| No. | Aerosol | Nozzle | | | Solvent (% by volume) | $KT_{50}$ (sec) | Solvent (% by volume) | $KT_{50}$ (sec) |
| Ex. 28 | 35 | Without | 2.02 | 19.43 | 3.33 | 44.9 | 3.3 | 133.1 |
| Ex. 29 | 36 | Without | 2.06 | 25.4 | 7.5 | 32.6 | 7.5 | 32 |
| Ex. 30 | 37 | With | 2.02 | 20.75 | 3.33 | 42.1 | — | — |
| Ex. 31 | 38 | With | 2.06 | 27.43 | 7.5 | 30.5 | — | — |
| Comp. Ex. 8 | 39 | Without | 2.13 | 9.18 | 3.33 | 102.4 | — | — |
| Comp. Ex. 9 | 40 | Without | 2.15 | 10.93 | 7.5 | 65 | — | — |
| Comp. Ex. 10 | 41 | Without | 2.2 | 14.37 | 15 | 36.5 | 15 | 38.2 |

It can be seen from the results of Table 5 that the aerosol 35 containing a small amount of a solvent is inferior in rapid action on German cockroach, but the aerosols 35 and 36 exhibit equivalent or more excellent disinsectization efficacy on house fly as compared with the aerosol 41 which is a standard prior product. It can be seen that the an aerosol 36 also has excellent disinsectization efficacy on German cockroaches as compared with the aerosol 41. In addition, when aerosols 35 and 36 are compared with the aerosols 39 and 40 containing an equivalent amount of a solvent, it is shown that disinsectization efficacy of the aerosols 39 and 40 is considerably low, and reduction in a solvent amount lowers harmful insect disinfesting effect, and at the same time, it is shown that superiority of constitutions of the present invention is remarkable. Here, for the aerosols 35 to 38, pollution due to an aerosol was not observed. In addition, it is seen that, when the presence or the absence of a long nozzle are compared, the presence of a long nozzle leads slightly more excellent efficacy in this Test Example.

Test Example 5

The above-mentioned aerosols 35 to 41 were evaluated for disinsectization efficacy in a quasi-field test. The test was performed by releasing test insects (50 house flies) into a 8-mat closed room (floor area of 13.2 m², height 2.5 m), and uniformly spraying an aerosol in the room so as to give a content of an active ingredient in the room of about 15 mg/8-mat closed room. Disinsectization efficacy of each aerosol was evaluated by obtaining $KT_{50}$ in the same manner as that of Test Example 2. A test was performed by repeating twice, and an average value was obtained. The results are shown in Table 6.

TABLE 6

| | | | House fly | |
| --- | --- | --- | --- | --- |
| No. | Aerosol | Nozzle | Solvent (% by volume) | $KT_{50}$ (sec) |
| Ex. 28 | 35 | Without | 3.33 | 250.8 |
| Ex. 29 | 36 | Without | 7.5 | 221.4 |
| Ex. 30 | 37 | With | 3.33 | 245.4 |
| Ex. 31 | 38 | With | 7.5 | 214.8 |
| Comp. Ex. 8 | 39 | Without | 3.33 | 510 |
| Comp. Ex. 9 | 40 | Without | 7.5 | 360 |
| Comp. Ex. 10 | 41 | Without | 15 | 280.2 |

It can be seen from the results of Table 6 that the aerosols 35 to 38 have excellent disinsectization efficacy as compared with the aerosol 41 which is a standard prior product. Since the present test is a test reflecting the actual use circumstance of an aerosol product, the results of the present test directly demonstrate efficacy of the aerosol of the present invention in actual use. The fact that $KT_{50}$ value for the aerosol 35 is more favorable than that of the aerosol 41 in the quasi-field test demonstrates that even if a solvent amount is reduced to about ⅕ compared to that of a standard prior product in practical use, sufficient efficacy comparable with that of an aerosol which is a standard prior product is maintained as far as constitutions of the present invention are adopted. In addition, by increasing an orifice diameter, or decreasing a container inner pressure to increase a particle diameter of a sprayed particle, efficacy of space spraying was rather increased than direct spraying. This is the result which cannot be expected from the previous findings, and this was thought to be the result of that adoption of constitutions of the present invention led to optimal control of a particle diameter regardless of reduction in a solvent, and not only insect adherability but also spatial diffusibility were improved. Here, for the aerosols 35 to 38, pollution due to a solvent was not observed. In addition, it is seen that when the presence or the absence of the long nozzle is compared, the presence of a long nozzle leads slightly more excellent efficacy in this Test Example.

Test Example 6

Aerosols 42 and 43 having prescribed aerosol compositions containing 0.15% by weight/volume of a disinfestant component (transfluthrin), a predetermined amount of a solvent (n-paraffin) shown in Table 7, and the balance a propellant (LPG), and having a container inner pressure [gauge pressure at 25° C.] of 0.15 MPa were prepared using an aerosol can having a content amount of 300 mL provided with an actuator without a long nozzle having an orifice diameter of 1.3 mm (Examples 32, 33). In addition, aerosols 44 to 46 were prepared according to the same manner except that an aerosol can having a content amount of 300 mL provided with an actuator without a long nozzle having an orifice diameter of 0.65 mm was used, and a container inner pressure was 0.42 MPa (Comparative Examples 11 to 13).

The resulting aerosols 42 to 46 were evaluated for disinsectization efficacy in the same manner as that of Test Example 4. Results are shown in Table 7. An amount of each aerosol to be sprayed to each test insect was adjusted so as to give an amount of an active ingredient shown in Table 7.

TABLE 7

| | | | Sprayed | | House fly | | | German cockroach | | |
| --- | --- | --- | --- | --- | --- | --- | --- | --- | --- | --- |
| No. | Aerosol | Nozzle | Spraying Amount (g/sec) | Particle Diameter (μm) | Active Ingredient (mg/time) | Solvent (% by volume) | $KT_{50}$ (sec) | Active Ingredient (mg/time) | Solvent (% by volume) | $KT_{50}$ (sec) |
| Ex. 32 | 42 | Without | 2.02 | 19.1 | 1.2 | 3.33 | 33.5 | 5 | 3.33 | 95.3 |
| Ex. 33 | 43 | Without | 2.06 | 24.08 | 1.2 | 7.5 | 30.4 | 5 | 7.5 | 51.6 |
| Comp. Ex. 11 | 44 | Without | 2.13 | 9.16 | 1.2 | 3.33 | 57.3 | 5 | 3.33 | 335.6 |
| Comp. Ex. 12 | 45 | Without | 2.15 | 10.95 | 1.2 | 7.5 | 41.9 | 5 | 7.5 | 218.3 |
| Comp. Ex. 13 | 46 | Without | 2.2 | 14.23 | 1.2 | 15 | 31.3 | 5 | 15 | 129.6 |

It can be seen from the results of Table 7 that the aerosols 42 to 43 are excellent in disinsectization efficacy as compared with the aerosols 44 to 46. In particular, on German cockroach, since aerosol 42 has a lower amount of a solvent as compared with the aerosol 46, it is usually thought that efficacy is remarkably reduced. However, it is seen that considerably excellent efficacy can be exhibited in aerosol 42 as compared to aerosol 46. For the aerosols 42 and 43, pollution due to an aerosol was not observed.

INDUSTRIAL APPLICABILITY

According to the present invention, there can be provided an aerosol for disinsectization having high disinsectization efficacy and low pollution property.

The invention claimed is:
1. An aerosol for disinsectization comprising a mixture comprising a disinfestant component, a solvent, and a propellant, and a pressure-resistant container provided with an actuator, wherein the mixture is contained in the pressure- resistant container having a pressure of from 0.15 to 0.4 MPa as expressed by a gauge pressure at 25° C.,
   wherein the solvent is contained in the mixture in an amount of from 0 to 8% by volume, and the actuator has an orifice diameter of from 0.7 to 2 mm; and
   wherein an average particle diameter of a particle comprising a sprayed aerosol content is from 19.1 to 27.43 μm (25° C.) at a position having a straight line distance from an orifice of 150 cm.

2. An aerosol for disinsectization comprising a mixture comprising a disinfestant component, a solvent, and a propellant, and a pressure-resistant container provided with an actuator, wherein the mixture is contained in the pressure-resistant container having a pressure of from 0.15 to 0.4 MPa as expressed by a gauge pressure at 25° C.,
   wherein the solvent is contained in the mixture in an amount of from 0 to 8% by volume, and the actuator has a long nozzle having an orifice diameter of from 0.4 to 2 mm; and
   wherein an average particle diameter of a particle comprising a sprayed aerosol content is from 19.1 to 27.43 μm (25° C.) at a position having a straight line distance from an orifice of 150 cm.

3. The aerosol according to claim 1, wherein a spraying amount at 25° C. is from 0.8 to 3 g/sec.

4. The aerosol according to claim 1, wherein the solvent is a paraffinic hydrocarbon.

5. The aerosol according to claim 1, wherein the disinfestant component is at least one member selected from the group consisting of metofluthrin, phthalthrin, d-T80-phthalthrin, d,d-T80-prallethrin, d,d-T98-prallethrin, d-T80-resmethrin, transfluthrin, imiprothrin, cyphenothrin and d,d-T-cyphenothrin.

* * * * *

UNITED STATES PATENT AND TRADEMARK OFFICE
CERTIFICATE OF CORRECTION

PATENT NO. : 8,568,688 B2  Page 1 of 1
APPLICATION NO. : 10/564156
DATED : October 29, 2013
INVENTOR(S) : Shingo Fujii et al.

It is certified that error appears in the above-identified patent and that said Letters Patent is hereby corrected as shown below:

ON THE TITLE PAGE:

Insert the following:

--(30)   Foreign Application Priority Data

Aug. 8, 2003    (JP)    ........................ 2003-290741--.

Signed and Sealed this
Eighth Day of April, 2014

Michelle K. Lee
*Deputy Director of the United States Patent and Trademark Office*